United States Patent
Tsukuda (10) Patent No.: US 7,830,520 B2
(45) Date of Patent: Nov. 9, 2010

(54) OPTICAL MEASUREMENT DEVICE FOR TRACE LIQUID SAMPLE

(75) Inventor: Yasuo Tsukuda, Mishima-gun (JP)

(73) Assignee: Shimadzu Corporation, Kyoto (JP)

( * ) Notice: Subject to any disclaimer, the term of this patent is extended or adjusted under 35 U.S.C. 154(b) by 237 days.

(21) Appl. No.: 12/293,341

(22) PCT Filed: Apr. 3, 2006

(86) PCT No.: PCT/JP2006/307032
§ 371 (c)(1),
(2), (4) Date: Sep. 17, 2008

(87) PCT Pub. No.: WO2007/113895
PCT Pub. Date: Oct. 11, 2007

(65) Prior Publication Data
US 2009/0073435 A1    Mar. 19, 2009

(51) Int. Cl.
*G01N 21/00* (2006.01)
*G01N 1/10* (2006.01)
(52) U.S. Cl. ................................. 356/440; 356/246
(58) Field of Classification Search ............... None
See application file for complete search history.

(56) References Cited
U.S. PATENT DOCUMENTS
5,945,334 A    8/1999    Besemer et al.

2004/0156748 A1    8/2004    Yamakawa et al.

FOREIGN PATENT DOCUMENTS

| EP | 1 447 669 A2 | 8/2004 |
|---|---|---|
| JP | 10-505410 A | 5/1998 |
| JP | 2004-239697 A | 8/2004 |
| JP | 2004-340791 A | 12/2004 |
| WO | 95/33846 A1 | 12/1995 |

OTHER PUBLICATIONS

NanoDrop ND-1000 Overview (online), NanoDrop Technologies LLC, U.S., Searched on Mar. 15, 2006, on the Internet <URL: http://www.nanodrop.com/nd-1000-overview.html>.

*Primary Examiner*—Gregory J Toatley, Jr.
*Assistant Examiner*—Amanda H Merlino
(74) *Attorney, Agent, or Firm*—Sughrue Mion, PLLC (57) ABSTRACT

In a spectrophotometer for measuring transmitted light of a trace liquid sample, four sample holders 12 are provided on a disk-like sample plate 11 while spaced apart by 90 degrees. The sample plate 11 is driven to rotate so that each of the sample holders 12 is sequentially moved to a sample supply position U1, a measuring position U2, a wiping position U3 and a waiting position U4. At the sample supply position U1, a trace amount of the liquid sample is dropped into a groove of the sample holder 12. Then at the measuring position U2, a window plate 22 is lowered onto the groove so as to determine the optical path length. Next, measurement of the transmitted light is performed. Further, while the sample holder 12 moves from the measuring position U2 to the waiting position U4, the liquid sample is absorbed and removed by contact with a cleaning pad 26. The liquid sample attached to the window plate 22 is wiped out by another pad. Since the operation to wipe off the measured sample is automatically performed, it is possible to improve the throughput of the measurement.

13 Claims, 4 Drawing Sheets

(a) IN MEASUREMENT (b) IN WIPING

(a) IN MEASUREMENT　　　(b) IN WIPING

Fig. 6

|  | 1回目 | 2回目 | 3回目 | 4回目 | 5回目 | ---- |
|---|---|---|---|---|---|---|
| SAMPLE HOLDER 12a | SAMPLE DROPPING | MEASURE-MENT | WIPING | WAITING | SAMPLE DROPPING | ---- |
| SAMPLE HOLDER 12b |  | SAMPLE DROPPING | MEASURE-MENT | WIPING | WAITING | ---- |
| SAMPLE HOLDER 12c |  |  | SAMPLE DROPPING | MEASURE-MENT | WIPING | ---- |
| SAMPLE HOLDER 12d |  |  |  | SAMPLE DROPPING | MEASURE-MENT | ---- |

OPTICAL MEASUREMENT DEVICE FOR TRACE LIQUID SAMPLE

TECHNICAL FIELD

The present invention relates to an optical measurement device for measuring a liquid sample by irradiating the liquid sample with light and measuring the transmitted light. The present invention especially relates to an optical measurement device, such as a spectrophotometer, for measuring the transmission characteristics of a trace liquid sample.

BACKGROUND ART

When a liquid sample is analyzed to measure the transmission characteristics such as transmittance and absorbency, by a spectrophotometer such as an ultraviolet-visible spectrophotometer, a prism or cylindrical-shaped cuvette for holding the liquid sample is normally used. An inner volume of a cuvette is normally several milliliters or more, and thus it is necessary to prepare a liquid sample in a sufficient amount to fill the cuvette.

Recently, an ultraviolet-visible spectrophotometer has been often used for determining protein or DNA quantity in the field of biochemistry. However, in many cases, the amount of a liquid sample to be analyzed is extremely small. Especially, since samples are precious and expensive in a DNA-related analysis, it is sometimes necessary to analyze a liquid sample in an amount of less than several microliters. Therefore, the aforementioned cuvette cell cannot be used for the analysis of a trace liquid sample.

Figure 8:
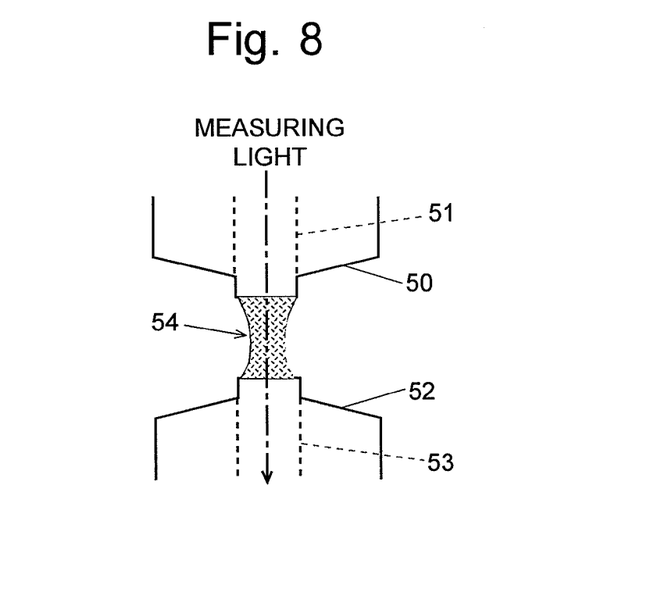
FIG. 8 is an explanatory view illustrating a conventional method of holding a trace liquid sample.

As a device for spectrophotometric analysis of a trace liquid sample, Spectrophotometer ND-1000 distributed by NanoDrop Technologies LLC is conventionally known (see Non-Patent Document 1). As shown in FIG. 8, the spectrophotometer is configured such that a liquid sample 54 bridges, owing to the surface tension, the space between an upper base portion 50 and a lower base portion 52, which are vertically provided face to face with a predetermined distance in between. A measuring light irradiated from a light emitting-side optical fiber 51 installed in the upper base portion 50 is allowed to pass through the liquid sample 54 and the transmitted light is received by a light receiving-side optical fiber 53 installed in the lower base portion 52. The optical path length in the liquid sample 54 is set to approximately 1 mm, and hence analysis of a liquid sample in a trace amount of approximately 1 to 2 µL is said to be possible.

However, according to the aforementioned conventional spectrophotometer, after the analysis of one sample, it is necessary for cleaning purposes to wipe the end faces of both the light emitting-side optical fiber and the light receiving-side optical fiber by using, for example, a laboratory paper, before analysis of a next sample. This operation is a troublesome task, because it needs to be performed manually every time analysis of one sample is finished. Moreover, there is a problem of low throughput, since it is not possible to measure a plurality of samples while automatically changing the samples.

Non-Patent Document 1: NanoDrop ND-1000 Overview (online), NanoDrop Technologies LLC, U.S., searched on Mar. 15, 2006 on the Internet <URL: http://www.nanodrop.com/nd-1000-overview.html>

DISCLOSURE OF THE INVENTION

Problems to be Solved by the Invention

To solve the aforementioned problems, the present invention intends to provide an optical measurement device for a trace liquid sample, which can perform a high-throughput transmission measurement of a liquid sample in a trace amount of approximately 1 to 2 µL or less, without troublesome manual operations.

Means for Solving the Problems

To solve the problems mentioned earlier, an optical measurement device according to the present invention is capable of measuring transmission characteristics of a trace liquid sample by irradiating the liquid sample with light and measuring transmitted light having passed through the liquid sample, and is characterized by having (a) a flat supporting plate which has, on an upper surface thereof, a plurality of sample holders with a transparent part in at least a lower portion thereof, and is capable of holding the liquid sample dropped therein;

(b) a moving mechanism which moves the supporting plate so that each of the sample holders provided on the supporting plate moves sequentially at least between a measuring position and a sample supply position;

(c) a sample supply section which drops the liquid sample into the sample holder at the sample supply position;

(d) a transparent suppressing plate which is movably provided above the sample holder to form an upper interface between itself and the sample in parallel with a bottom surface of the liquid sample held in the sample holder at the measuring position;

(e) a light measuring section which irradiates the liquid sample with a measuring light from above or from below, the liquid sample being held in a space surrounded by the sample holder and a lower surface of the suppressing plate, and measures the light transmitting through the liquid sample at the measuring position;

(f) a first wiping mechanism which contacts the sample holder to wipe off the liquid sample, in a path of movement of the sample holder having been measured at the measuring position and moved by the moving mechanism from the measuring position to the sample supply position; and (g) a second wiping mechanism which contacts the lower surface of the suppressing plate to wipe off the liquid sample after completion of the measurement by the light measuring section.

The sample holder may be, for example, a groove having a flat bottom surface. The groove may be formed by carving the upper surface of a plate-like base body, or may be formed by attaching a plate-like member having an opening to the upper surface of the plate-like body, or may be formed by attaching two plate-like members, with a predetermined space between them, to the upper surface of the plate-like body. Moreover, the sample holder may be a protrusion having a flat upper surface, which rises above the upper face of the sample holder. In any of the aforementioned cases, the sample holder needs to have a configuration in which the bottom surface is flat and a portion below the bottom surface is transparent.

Effect of the Invention

In the optical measurement device according to the present invention, when one of the plurality of sample holders is located at the sample supply position, the sample supply section drops a trace amount of a liquid sample into the sample holder. The dropped liquid sample forms a swelling liquid drop due to surface tension, for example, in the groove or on the upper surface of the protrusion. Thereafter, when the moving mechanism moves the supporting plate so that the sample holder comes to the measuring position, the suppressing plate is moved to cover the liquid drop held in the sample holder, with the result that the liquid sample is filled in the space between the lower surface of the suppressing plate and the bottom surface of the sample holder. In this state, the light measuring section irradiates the liquid sample with a measuring light and then measures the transmitted light. The distance from an upper surface corresponding to the interface between the liquid sample and the suppressing plate to a bottom surface corresponding to the interface between the liquid sample and the sample holder is determined to be the optical path length in the liquid sample.

When the measurement is completed, the moving mechanism moves the supporting plate so that the sample holder moves from the measuring position to the sample supply position. On the path of movement, a first wiping mechanism is installed. The sample holder contacts the first wiping mechanism, or the sample holder slides while keeping contact with the first wiping mechanism, thereby the liquid sample held by the sample holder is wiped off by the first wiping mechanism. Thereafter, the sample holder returns to the sample supply position in a state where a liquid sample as a next measurement object can be dropped into the sample holder. On the other hand, when the measurement by the light measuring section is completed, the second wiping mechanism wipes off the residue of the liquid sample attached to the lower surface of the suppressing plate so as to prepare for the next measurement.

The above operation is sequentially and repeatedly performed on each of the plurality of the sample holders, and at the same time different operations simultaneously progress in such a manner that, for example, when the measurement is performed on a first sample holder, a liquid sample is dropped into a second sample holder, and further the first wiping mechanism wipes off a measured liquid sample in a third sample holder.

As previously mentioned, according to the optical measurement device for a trace liquid sample of the present invention, the operation of removing the unnecessary measured liquid sample is automatically performed in conjunction with the switching of the positions of the sample holders along with the movement of the supporting plate. Therefore, an operator does not need to do some troublesome tasks such as the wiping of a sample, and thereby labor savings can be achieved. On the other hand, since each of a series of operations from the supply (dropping) through the measurement to the removal of a liquid sample is automatically and cyclically performed, it is possible to improve measurement throughput and thus it is possible to treat a large amount of samples in a relatively short period of time.

Moreover, one of the embodiments of the present invention may have a configuration in which the moving mechanism drives the supporting plate to rotate around a vertical axis, and the plurality of sample holders are disposed on a circle centering the vertical axis. In this configuration, one of the sample holders is moved from the measuring position to the sample supply position as the supporting plate rotates in one direction, and the first wiping mechanism is disposed on the path of movement.

This configuration can be easily achieved by properly disposing the light measuring section, the sample supply section, and the first wiping mechanism around the axis of rotation as a center, and further a conventional motor can be used as the moving mechanism that drives the supporting plate to rotate in one direction. Due to this simple structure, the cost can be reduced.

Furthermore, in the above configuration, it is preferable that the first wiping mechanism be provided at a wiping position, and the moving mechanism intermittently move the supporting plate so that one of the sample holders provided on the supporting plate sequentially moves and stops from the sample supply position to the measuring position to the wiping position, one position after the other. In this case, preferably, the plurality of the sample holders provided on the supporting plate are each sequentially moved from the sample supply position to the measuring position to the wiping position one position after the other along with the intermittent movement of the supporting plate caused by the moving mechanism.

According to the above configuration, the device can operate without any wasteful motion since different operations are simultaneously performed on the plurality of sample holders. As a result, it is possible to improve the throughput by reducing the measurement intervals for the sequential measurement of a plurality of samples.

Furthermore, in one configuration of the present invention, the suppressing plate is vertically movable, and when the suppressing plate is stopped at an upper position, the second wiping mechanism horizontally moves so as to wipe the lower surface of the suppressing plate. According to this configuration, it becomes possible to immediately wipe the liquid sample attached to the lower surface of the suppressing plate each time the measurement is completed.

BEST MODE FOR CARRYING OUT THE INVENTION

Figure 1:
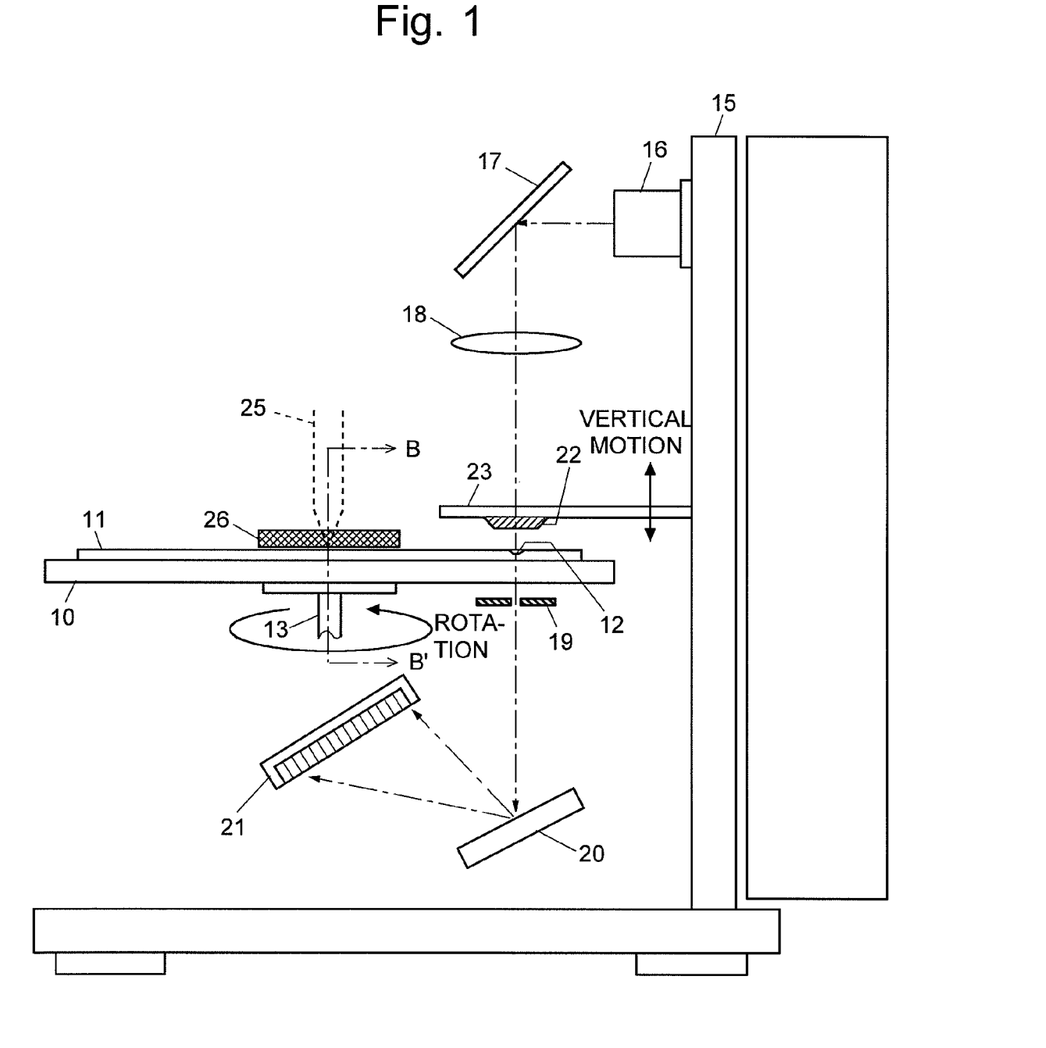
FIG. 1 is a schematic structural diagram illustrating an ultraviolet-visible spectrophotometer according to one embodiment of the present invention.

The following description will discuss an ultraviolet-visible spectrophotometer as one embodiment of the optical measurement device for trace liquid sample according to the present invention. FIG. 1 is a side view illustrating a schematic structure of the ultraviolet-visible spectrophotometer according to the present embodiment.

In FIG. 1, a disk-like sample plate 11 (corresponding to the supporting member of the present invention) having thereon four sample holders 12 for holding the liquid sample is loaded onto a disk-like sample table 10 which extends in a substantially horizontal plane. The sample plate 11 integrated with the sample table 10 can be rotated by a driving mechanism (corresponding to the moving mechanism of the present invention) including a motor or other members, not shown in FIG. 1, around a rotation axis 13 as the center within a substantially horizontal plane. The sample table 10 has an opening beneath each of the four sample holders 12.

Light is outputted in a substantially horizontal direction from a light source 16 installed at an upper portion of an upright supporting pole 15. The direction of the light is changed to immediately below by a plain mirror 17, and then condensed by a condensing lens 18 to be used as a measuring light. The measuring light is then irradiated to the liquid sample from substantially right above the sample held by the sample holder 12, that is located at a measuring position to be described later. The measuring light passes through the liquid sample as a transmitted light in a downward direction, and in a slit 19 disposed thereunder, the light range of the transmitted light is limited and then introduced into a diffraction grating 20. In the diffraction grating 20, the transmitted light is wavelength-dispersed and diffused, and the diffused wavelength-dispersed light is detected all together by a multi-channel detector 21 such as a CCD linear sensor (those structural elements correspond to the light measuring section of the present invention).

A window plate 22 having a transparent part is provided in a light path between the condenser lens 18 and the sample plate 11. The window plate 22 (corresponding to the suppressing section of the present invention) is held by a window plate holder 23 which is vertically movable along the supporting pole 15. Although the lower surface of the window plate 22 is separated from the upper surface of the sample plate 11 in FIG. 1, in actual measurements, the lower surface of the window plate 22 contacts the upper surface of the sample plate 11.

Figure 2:
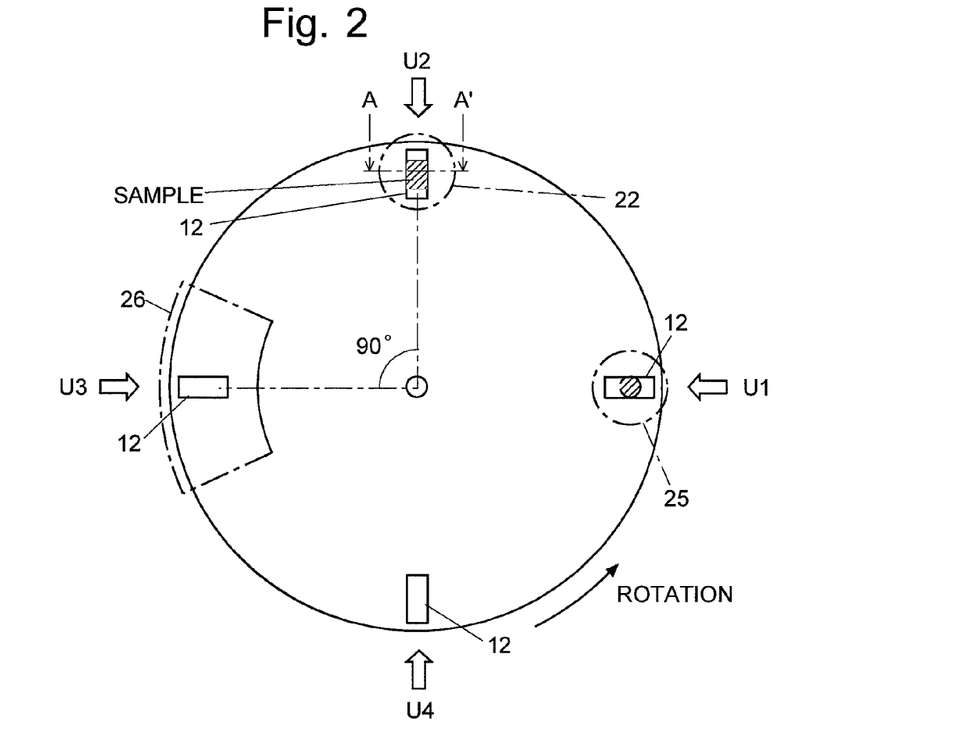
FIG. 2 is a view illustrating an upper surface of a sample plate and members disposed above the sample plate in the ultraviolet-visible spectrophotometer of the present embodiment.
Figure 3:
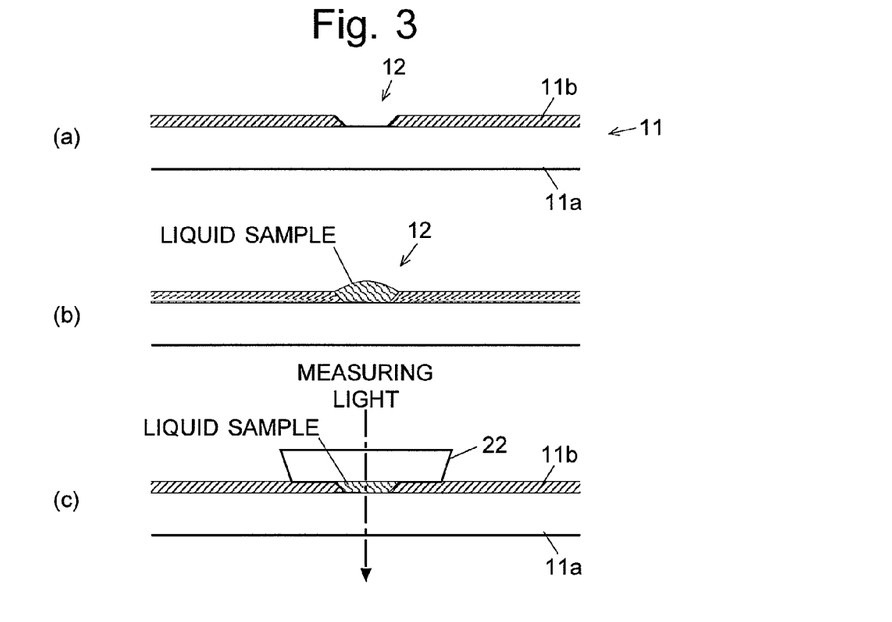
FIGS. 3(a), 3(b), and 3(c) are views illustrating a cross-section at arrow line A-A' in FIG. 2.
Figure 4:
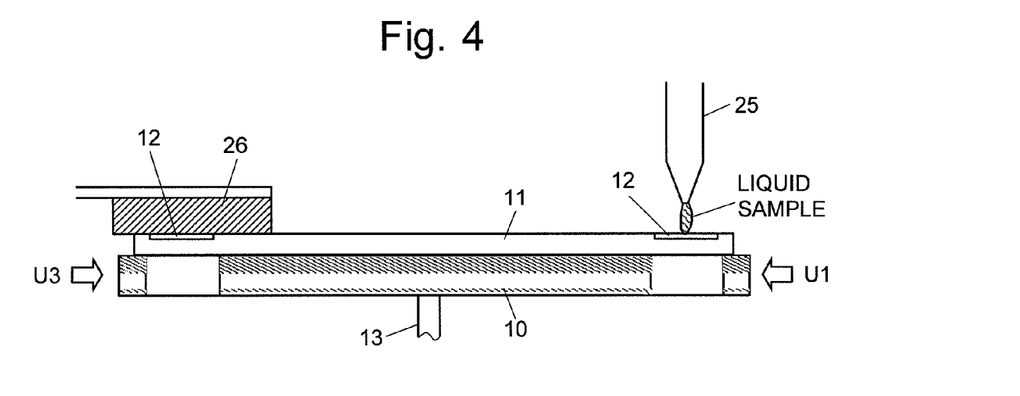
FIG. 4 is an end view at arrow line B-B' in FIG. 1.

FIG. 2 is a view illustrating a positional relationship between the upper surface of the sample plate 11 and members disposed above the surface, FIG. 3 illustrates a cross-sectional view at arrow line A-A' in FIG. 2, and FIG. 4 illustrates an end view at arrow line B-B' in FIG. 1. As shown in FIG. 2, at positions close to the circumference on the disk-like sample plate 11, four sample holders 12 are arranged in a concentric circle centering a rotation axis 13, while spaced apart by 90 degrees.

As shown in FIG. 3(a), the sample plate 11 is configured by attaching a thin light-shielding member 11b, which is made of a light-shielding material such as metal and has a long rectangular opening formed therein in the diameter direction, on the upper surface of a thin plate-like base 11a made of a material with a high light transmittance such as quarts glass. The peripheral edge of the opening is substantially V-shaped in depthwise. Accordingly, a groove having a trapezoidal vertical cross section (the bottom side is shorter than the upper side) and a long rectangular shape in the diameter direction of the sample plate 11 is formed on the base 11a, and the groove functions as the sample holder 12. The inner surface of the opening in the light-shielding member 11b corresponds to a side surface of the sample holder 12, and the upper surface of the base 11a corresponds to the bottom surface of the sample holder 12.

As previously mentioned, the sample plate 11 is driven to rotate around the rotation axis 13 as the center, and on the orbits of the movements of the sample holders 12 along with the rotation, four positions are fixed. In other words, a measuring position U2 is provided directly below the window plate 22; a sample supply position U1 is provided at a position 90 degrees backward from the measuring position U2; a wiping position U3 is provided at a position 90 degrees forward from the measuring position U2; and a waiting position U4 is provided at a position facing the measuring position U2, while spaced apart therefrom by 180 degrees.

The sample plate 11 is designed to intermittently rotate 90 degrees each time so that the four sample holders 12 stop at the four positions U1 to U4 for a predetermined time. Therefore, when attention is paid to one of the sample holders 12, the sample holder 12 sequentially moves from the sample supply position U1 to the measuring position U2, the wiping position U3 and the waiting position U4, and thereafter comes back again to the sample supply position U1 to repeat this cycle. On the other hand, as for the state at a certain time point, one of the sample holders 12 is located at the sample supply position U1, another is located at the measuring position U2, another is located at the wiping position U3, and the other is located at the waiting position U4. Therefore, every time the sample plate 11 is rotated by 90 degrees, the sample holder 12 located at each of the positions U1 to U4 is switched one after another.

The window plate 22 and the diffraction grating 20 are respectively present above and below the measuring position U2. Besides them, as shown in FIG. 4, a sample dropping portion 25 for dropping a trace liquid sample is provided above the sample supply position U1. Further, a cleaning pad 26 (corresponding to the first wiping mechanism of the present invention) made of an absorbent material such as a nonwoven fabric, which is pressed with an appropriate amount of pressure against the upper surface of the sample plate 11, is provided above the wiping position U3. Practically, the cleaning pad 26 is provided not only at the wiping position U3 but is also disposed so as to cover a certain wide range including the vicinity of the position U3, as shown in FIG. 2.

Although not shown in the figure, the sample dropping portion 25 has a structure capable of sampling and dropping a plurality of prepared liquid samples in a predetermined order. The dropping amount is less than several microliters, and preferably a trace amount of not more than 1 to 2 microliters.

The following description will discuss the analysis operation using the ultraviolet-visible spectrophotometer of the present embodiment. First, one of the sample holders 12 on the sample plate 11 is focused for the explanation. At the time when the sample holder 12 is located at the waiting position U4, liquid sample residue inside the groove of the sample holder 12 has been completely wiped out in the previous wiping operation. A 90 degrees rotation of the sample plate 11 (with the sample table 10) from this position transfers the sample holder 12 to the sample supply position U1, where the sample dropping portion 25 drops a prescribed amount of the prepared liquid sample. The dropped liquid sample does not spread so much in the groove of the sample holder 12 due to surface tension, but instead keeps a swelling, sphere-like drop form as shown in FIG. 3(b).

Next, a further 90 degrees rotation of the sample plate 11 from this state transfers the sample holder 12 to the measuring position U2. During the movement, the window plate 22 has been withdrawn by the window holder 23 at an upper position, and thus the lower surface of the window plate does not contact the upper surface of the sample plate 11 and the liquid sample. When the rotation of the sample plate 11 is paused, the window plate 22 is moved downward until it reaches a position where the lower surface of the window plate 22 slightly touches the upper surface of the sample plate 11 as shown in FIG. 3(c). Upon being pressed by the window plate 22, an excessive, swelling portion of the liquid sample spreads to flow in a longitudinal direction (i.e. the diameter direction of the sample plate 11) of the sample holder 12. Accordingly, the liquid sample fills the space having a trapezoidal cross section formed in the groove of the sample holder 12 and the lower surface of the window plate 22 at a position where the measuring light passes through the liquid sample.

In this state, as previously mentioned, the measuring light is irradiated from the right above to the vertical below so that the optical axis of the measuring light passes through the center and its vicinity of the sample holder 12. The transmitted light that has passed through the liquid sample filled in the substantially trapezoidal space as mentioned above exits right below to pass through a slit 19. Thus, the depth of the groove of the sample holder 12 becomes the optical path length of the sample holder 12. In this manner the optical path length is uniquely decided regardless of the amount of the firstly dropped liquid sample. Since a specific wavelength component in the measuring light is absorbed by the liquid sample, processing the light intensity signal for each of the wavelengths concurrently detected by a detector 21 in a signal processor, which is not shown in the figures, makes it possible to generate a spectrum reflecting the transmission characteristics of the liquid sample. It is to be noted that, due to the light-shielding member 11b which covers areas other than the area where the liquid sample exists, even if the diameter of the measuring light irradiated to the upper surface of the sample plate 11 is larger than the width of the groove of the sample holder 12, the area outside the groove is shielded by the light-shielding member 11b.

Upon finishing the import of the light intensity signals obtained by the detector 21, the measurement is completed. Then, the window plate holder 23 moves the window plate 22 upward, and the sample plate 11 is rotated 90 degrees to transfer the sample holder 12 to the wiping position U3. As mentioned earlier, practically, before the sample holder 12 reaches to the wiping position U3, the sample holder 12 makes contact with the lower surface of the cleaning pad 26 and slides thereon, allowing the liquid sample in the groove of the sample holder 12 to be absorbed by the cleaning pad 26. Then, while the sample holder 12 stays at the wiping position U3 for an interim period, the liquid sample is further absorbed and finally completely removed.

Figure 5:
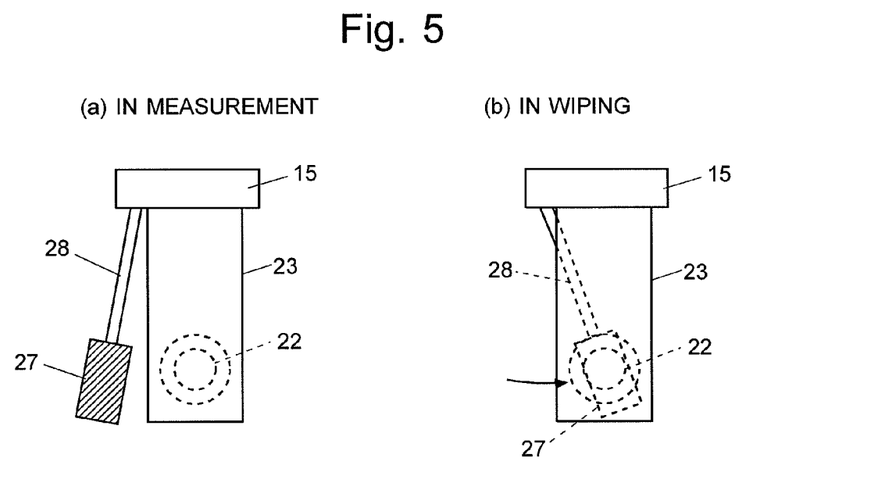
FIGS. 5(a) and 5(b) are schematic upper surface views illustrating the structure of a cleaning pad for wiping a window plate.

On the other hand, when the window plate 22 shifting upwards stops at an elevated position along with the completion of the measurement, an arm 28 having been withdrawn at a lateral side sways in conjunction with the rotational movement of the sample plate 11 as shown in FIGS. 5(a) and 5(b). As a result, the upper surface of a cleaning pad 27 (corresponding to the second wiping mechanism of the present invention), which is made of a similar material as the aforementioned cleaning pad 26 and is provided at an end portion of the arm 28, makes contact with the lower surface of the window plate 22 and then slides on the surface. Although the liquid sample has also been attached to the lower surface of the window plate 22 during the foregoing measurement, the residue of the liquid sample is wiped off as a result of the sliding. The operation of wiping off the lower surface of the window plate 22 is performed in a period when the sample holder 12 having been measured moves from the measuring position U2 to the wiping position U3. This operation removes the measured liquid sample from both the sample holder 12 and window plate 22.

Next, a further 90 degree rotation of the sample plate 11 transfers the sample holder 12 from the wiping position U3 to the waiting position U4, and after staying for an interim period at the waiting position U4, the sample holder 12 moves to the sample supply position U1. In this manner, the operations as previously mentioned are repeated.

Figure 6:
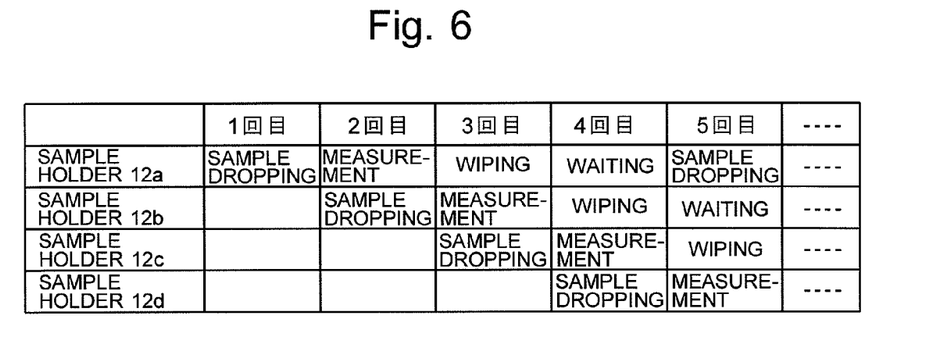
FIG. 6 is a table showing the operational shifts of four sample holders.

The preceding description detailed the series of operations by focusing on one of the sample holders 12 on the sample plate 11. However, actually the four sample holders 12 are provided at angular intervals of 90 degrees, and the four positions U1 to U4 including the sample supply position U1 are also provided at angular intervals of 90 degrees, allowing the operations to be simultaneously and cyclically performed on the four sample holders 12 at each of the positions U1 to U4. Namely, when the four sample holders are labeled as 12a to 12d, the operations performed on each of the sample holders 12a to 12d each time the sample plate 11 rotates 90 degrees are as illustrated in FIG. 6. In this manner, one of the liquid samples can be measured each time the sample plate 11 rotates 90 degrees, and thus it is possible to efficiently perform a continuous analysis by reducing the spare time when no measurement is performed.

Figure 7:
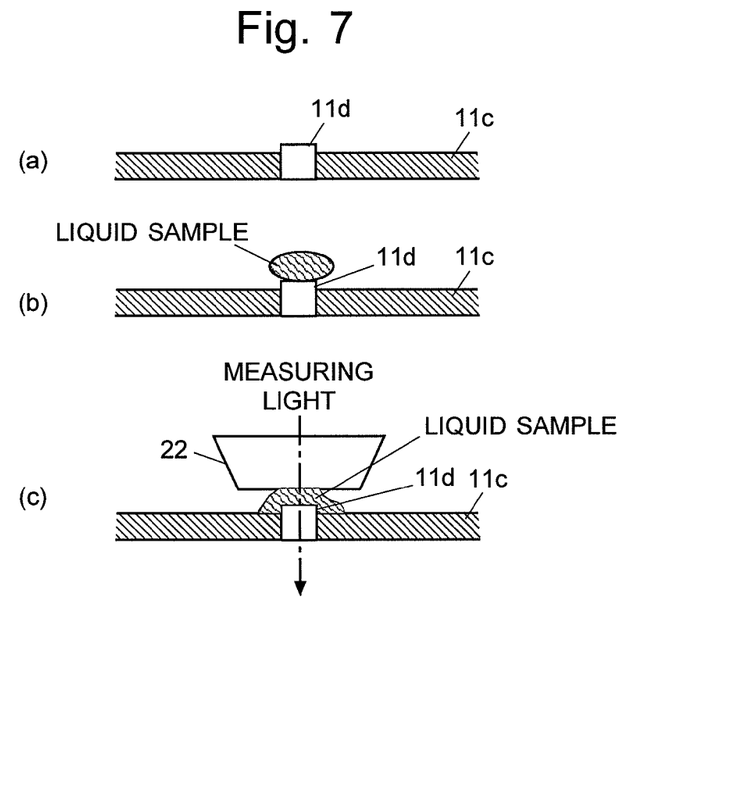
FIGS. 7(a), 7(b), and 7(c) are cross-sectional views each illustrating another embodiment of the sample holder on the sample plate.

FIGS. 7(a), 7(b), and 7(c) are cross-sectional views each illustrating another embodiment of the sample holder 12 provided on the sample plate 11. As shown in FIG. 7(a), a round through hole is formed in a vertical direction in a disk-like base table 11c made of a material having light-shielding properties. A cylindrical body 11d made of a transparent material is inserted in the through hole and held therein. The flat bottom surface of the cylindrical body 11d is arranged to be flush with the lower surface of the base table 11c, and the flat upper surface of the cylindrical body 11d rises above the upper surface of the base table 11c. As shown in FIG. 7(b), a trace amount of the liquid sample is dropped onto the upper surface of the cylindrical body 11d, and the dropped liquid sample becomes spherical due to the surface tension.

From above the sample, the window plate 22 is lowered to the position where the distance between the lower surface of the window plate 22 and the upper surface of the cylindrical body 11d is a predetermined distance. As shown in FIG. 7(c), when the liquid sample is pressed by the window plate 22, the spherical liquid drop is deformed and spread while a narrow space between the lower surface of the window plate 22 and the upper surface of the cylindrical body 11d is filled in with the liquid sample 11. In this manner as well, the optical path length of the measuring light in the liquid sample is determined, and by measuring the transmitted light that has passed through the bottom of the cylindrical body 11d, it is possible to perform a transmission measurement that is almost the same as the aforementioned measurement. The sample holder 12 having an upwardly protruding structure as in the present embodiment is advantageous in that the wiping of the liquid sample with the cleaning pad is easier, as compared with the groove-shaped sample holder.

In addition to the previous example, it is possible to form the sample holder 12 by attaching two sheets of plate-like spacers made of a material having light-shielding properties, with a predetermined distance therebetween, onto a thin, plate-like base table made of a material having a good light transparency, such as silica glass. In this structure, the space between the two spacers in a concave shape functions like the previously described groove.

It is to be noted that the previous example is just one of the examples of the present invention, and an appropriate change, modification, and addition may be applied thereto within the scope of the present invention.

For example, the cleaning pads 26 and 27 are not necessarily a so-called dry wiping material having absorbability (water-absorbing property), but may be a so-called wet wiping material containing water or a prescribed solvent, or may be a combination of a dry wiping mechanism and a wet wiping mechanism. Further, as is clear from the above explanation, since any operation is not performed at the waiting position U4 on the sample holder 12, the wiping operation may also be carried out at the position U4.

Moreover, since dirty cleaning pads 26 and 27 may cause contamination, it is possible to include an automatic feeder of the absorbent material such as nonwoven fabric so as to prevent the absorbent that has been used for the absorption of the liquid sample from being reused.

Further, the number and the arrangement of the sample holders 12 on the sample plate 11 described in the example are just an example, and of course, a proper change can be made. Furthermore, the sample plate may be configured, for example, to move back and forth along a straight line or an arc, instead of the rotation on the sample plate 11.

The invention claimed is:

1. An optical measurement device for measuring transmission characteristics of a trace liquid sample by irradiating the liquid sample with measuring light and measuring transmitted light having passed through the liquid sample, the optical measurement device comprising:
   (a) a flat supporting plate which has, on an upper surface thereof, a plurality of sample holders with a transparent part in at least a lower portion thereof, and is capable of holding the liquid sample dropped therein;
   (b) a moving mechanism which moves the supporting plate so that each of the sample holders provided on the supporting plate moves sequentially at least between a measuring position and a sample supply position;
   (c) a sample supply section which drops the liquid sample into the sample holder at the sample supply position;
   (d) a transparent suppressing plate which is movably provided above the sample holder to form an upper interface between itself and the sample in parallel with a bottom surface of the liquid sample held in the sample holder at the measuring position;
   (e) a light measuring section which irradiates the liquid sample with a measuring light from above or from below, the liquid sample being held in a space surrounded by the sample holder and a lower surface of the suppressing plate, and measures the light transmitting through the liquid sample at the measuring position;
   (f) a first wiping mechanism which contacts the sample holder to wipe off the liquid sample, in a path of movement of the sample holder having been measured at the measuring position and moved by the moving mechanism from the measuring position to the sample supply position; and
   (g) a second wiping mechanism which contacts the lower surface of the suppressing plate to wipe off the liquid sample after completion of the measurement by the light measuring section.

2. The optical measurement device for a trace liquid sample according to claim 1, wherein the sample holder is a groove having a flat bottom surface.

3. The optical measurement device for a trace liquid sample according to claim 1, wherein the sample holder is a protrusion having a flat upper surface, which rises above the upper face of the sample holder.

4. The optical measurement device for a trace liquid sample according to claim 1, wherein:
   the moving mechanism drives the supporting plate to rotate around a vertical axis;
   the plurality of sample holders are disposed on a circle centering the vertical axis so that one of the sample holders is moved from the measuring position to the sample supply position as the supporting plate rotates in one direction; and
   the first wiping mechanism is disposed on the path of movement.

5. The optical measurement device for a trace liquid sample according to claim 4, wherein:
   the first wiping mechanism is provided at a wiping position; and
   the moving mechanism intermittently moves the supporting plate so that one of the sample holders provided on the supporting plate sequentially moves and stops from the sample supply position to the measuring position to the wiping position, one position after another.

6. The optical measurement device for a trace liquid sample according to claim 5, wherein the plurality of the sample holders provided on the supporting plate are each sequentially moved from the sample supply position to the measuring position to the wiping position, one position after another, along with the intermittent movement of the supporting plate caused by the moving mechanism.

7. The optical measurement device for a trace liquid sample according to claim 1, wherein:
   the suppressing plate is vertically movable; and
   the second wiping mechanism horizontally moves to wipe a lower surface of the suppressing plate when the suppressing plate is stopped at an upper position.

8. The optical measurement device for a trace liquid sample according to claim 2, wherein:
   the moving mechanism drives the supporting plate to rotate around a vertical axis;
   the plurality of sample holders are disposed on a circle centering the vertical axis so that one of the sample holders is moved from the measuring position to the sample supply position as the supporting plate rotates in one direction; and
   the first wiping mechanism is disposed on the path of movement.

9. The optical measurement device for a trace liquid sample according to claim 3, wherein:
   the moving mechanism drives the supporting plate to rotate around a vertical axis;
   the plurality of sample holders are disposed on a circle centering the vertical axis so that one of the sample holders is moved from the measuring position to the sample supply position as the supporting plate rotates in one direction; and
   the first wiping mechanism is disposed on the path of movement.

10. The optical measurement device for a trace liquid sample according to claim 8, wherein:
    the first wiping mechanism is provided at a wiping position; and
    the moving mechanism intermittently moves the supporting plate so that one of the sample holders provided on the supporting plate sequentially moves and stops from the sample supply position to the measuring position to the wiping position, one position after another.

11. The optical measurement device for a trace liquid sample according to claim 9, wherein:
the first wiping mechanism is provided at a wiping position; and
the moving mechanism intermittently moves the supporting plate so that one of the sample holders provided on the supporting plate sequentially moves and stops from the sample supply position to the measuring position to the wiping position, one position after another.

12. The optical measurement device for a trace liquid sample according to claim 10, wherein the plurality of the sample holders provided on the supporting plate are each sequentially moved from the sample supply position to the measuring position to the wiping position, one position after another, along with the intermittent movement of the supporting plate caused by the moving mechanism.

13. The optical measurement device for a trace liquid sample according to claim 11, wherein the plurality of the sample holders provided on the supporting plate are each sequentially moved from the sample supply position to the measuring position to the wiping position, one position after another, along with the intermittent movement of the supporting plate caused by the moving mechanism.

* * * * *